United States Patent
Rees et al.

(10) Patent No.: US 9,454,557 B2
(45) Date of Patent: Sep. 27, 2016

(54) UNIT OF WORK BASED INCREMENTAL DATA PROCESSING

(71) Applicant: ORACLE INTERNATIONAL CORPORATION, Redwood Shores, CA (US)

(72) Inventors: John K. Rees, Brookline, MA (US); Rohit Chaturvedi, New Delhi (IN)

(73) Assignee: ORACLE INTERNATIONAL CORPORATION, Redwood Shores, CA (US)

( * ) Notice: Subject to any disclaimer, the term of this patent is extended or adjusted under 35 U.S.C. 154(b) by 117 days.

(21) Appl. No.: 14/158,964

(22) Filed: Jan. 20, 2014

(65) Prior Publication Data

US 2015/0066942 A1   Mar. 5, 2015

Related U.S. Application Data

(60) Provisional application No. 61/871,459, filed on Aug. 29, 2013.

(51) Int. Cl.
*G06F 17/30* (2006.01)
*G06F 19/00* (2011.01)

(52) U.S. Cl.
CPC ... *G06F 17/30336* (2013.01); *G06F 17/30368* (2013.01); *G06F 17/30418* (2013.01); *G06F 19/363* (2013.01)

(58) Field of Classification Search
CPC .................. G06F 17/30067; G06F 17/30286; G06F 17/30315; G06F 17/30336; G06F 17/30339; G06F 17/30451; G06F 17/30442; G06F 17/30448; G06F 17/30457; G06F 17/3046; G06F 17/30463; G06F 17/30466; G06F 17/30498; G06F 17/3051; G06F 17/30864; G06F 17/30368; G06F 17/30418; G06F 19/363

USPC ....... 707/624, 625, 713, 714, 717, 720, 741; 715/513

See application file for complete search history.

(56) References Cited

U.S. PATENT DOCUMENTS

| | | | | |
|---|---|---|---|---|
| 5,832,527 A * | 11/1998 | Kawaguchi | ....... | G06F 17/30067 |
| 6,519,587 B1 * | 2/2003 | Blinn | ................ | G06F 17/30421 |
| | | | | 707/623 |
| 6,519,601 B1 * | 2/2003 | Bosch | ............... | G06F 17/30339 |
| 8,725,734 B2 * | 5/2014 | Boh | .......................... | G06F 7/08 |
| | | | | 707/737 |
| 2005/0055369 A1 * | 3/2005 | Gorelik | ............. | G06F 17/30292 |
| 2007/0006070 A1 * | 1/2007 | Baartman | .......... | G06F 17/30448 |
| | | | | 715/234 |
| 2007/0192304 A1 * | 8/2007 | Iyer | .................... | G06F 17/30463 |
| 2007/0250473 A1 * | 10/2007 | Larson | ............. | G06F 17/30457 |
| 2008/0059468 A1 * | 3/2008 | Bender | ............. | G06F 17/30442 |
| 2013/0151535 A1 * | 6/2013 | Dusberger | ........ | G06F 17/30336 |
| | | | | 707/747 |
| 2014/0067790 A1 * | 3/2014 | Lipin | ................ | G06F 17/30595 |
| | | | | 707/714 |

* cited by examiner

*Primary Examiner* — Greta Robinson
(74) *Attorney, Agent, or Firm* — Kraguljac Law Group, LLC

(57) ABSTRACT

Systems, methods, and other embodiments associated with a unit of work for incremental data processing are described. In one embodiment, a method includes selecting a unit of work key for a program that processes records in a source table. The unit of work key is selected such that modifications to a record having a certain unit of work key value will not affect the program's processing of records having a different unit of work key value. The selected unit of work key is associated with the program. When a record in the source table is created, modified, or deleted, a unit of work key value is identified for the record and a selected set of records having the identified unit of work key value is provided to the program. Thus, records in the data source that do not have the identified unit of work key values are not provided to the program.

45 Claims, 13 Drawing Sheets

UNIT OF WORK BASED INCREMENTAL DATA PROCESSING

CROSS REFERENCE TO RELATED APPLICATIONS

This disclosure claims the benefit of U.S. Provisional Patent Application Ser. No. 61/871,459 filed Aug. 29, 2013, titled "UNIT OF WORK BASED INCREMENTAL DATA PROCESSING", inventor: John K. Rees, and assigned to the present assignee.

BACKGROUND

In many data processing systems, there are data flows where a small subset of data changes each time the data flow is executed. For instance, in a clinical trial enrolling 10,000 subjects over the course of three years, in a given day only a small subset of the subjects have a change to their data. However, it is common for programs to access the clinical trial data to perform various derivations and transformations of the data on a daily or even hourly basis. As the size of the source data set increases, performing the derivations and transformations on the entire data set to update the results becomes impractical.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Figure 1:
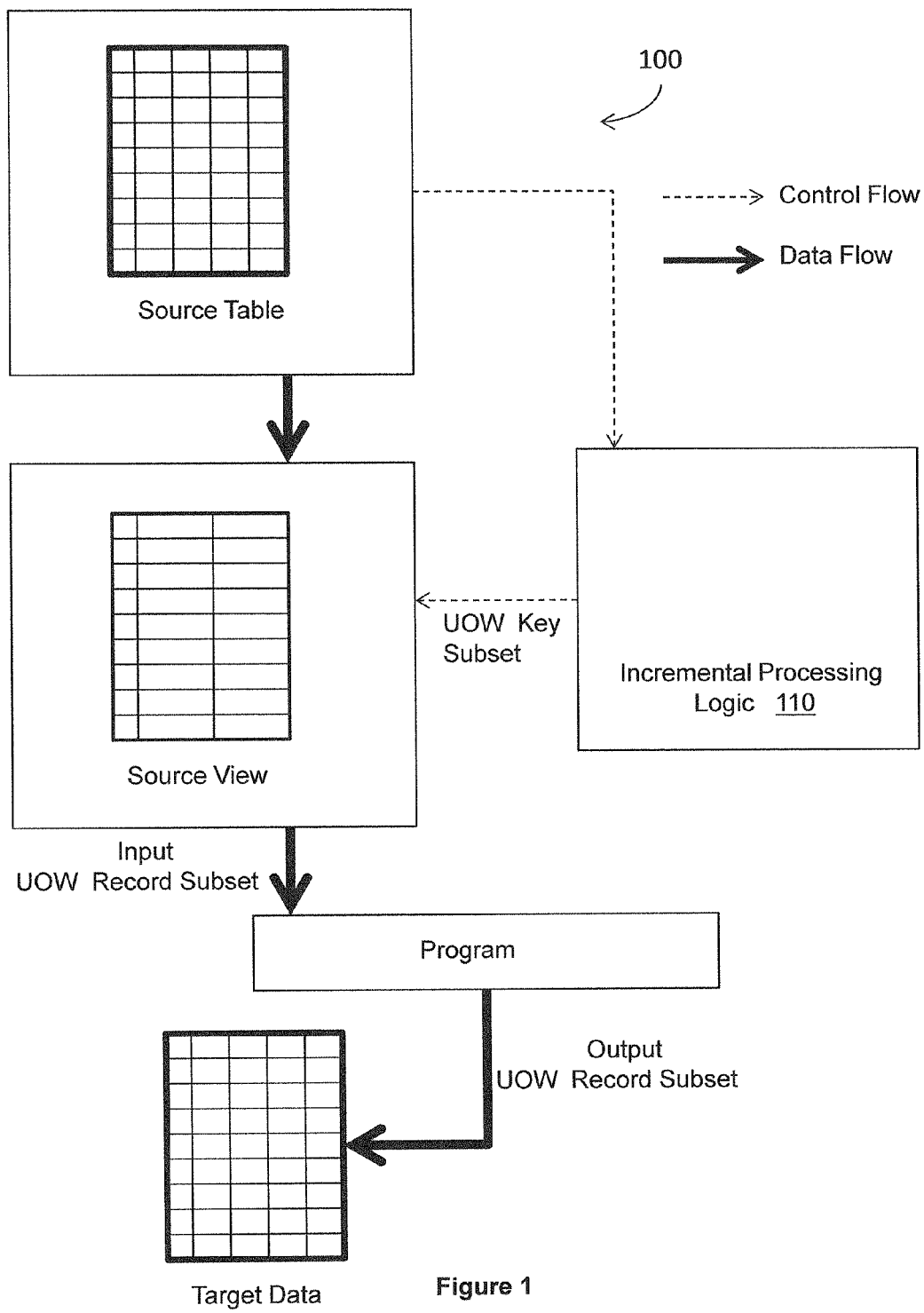
FIG. 1 illustrates one embodiment of a system associated with unit of work based incremental data processing.

In many instances it is desirable to frequently update the results of a program that processes data from source data. When the source data is extensive, and only a small subset of the source data for the program changes, re-running the program on the entire source data corpus becomes impractical. It is common for the changes within a particular sub-unit of data, like a subject or subject-visit in a clinical trial, to have an impact with respect to the program result that is limited to the sub-unit of data. For example, if a program processes clinical trial data for 10,000 subjects to produce an average blood pressure for each subject across all of the subjects' visits, a change to a given subject's blood pressure will not affect the average blood pressure for the other 9,999 subjects' average blood pressure. Thus, it is not necessary to re-run the program on the entire corpus of the 10,000 subjects' records to update the results of the program in the presence of a change to a single subject's data. The same holds true when any relatively small subset of source data is modified.

To address the problem of efficiently updating program results when a small subset of source data changes, custom detection techniques are sometimes employed in the individual programs that access the source data. It is difficult to support custom detection techniques when the programs are custom developed or when there is a mix of different programs accessing the same source data. This is because often it is not obvious what operations are being performed by the different programs, meaning that possible interactions between records as processed by the program are not apparent.

Systems and methods are described herein that facilitate incremental processing by allowing a unit of work (UOW) key to be specified for a program that accesses source data. The UOW key reflects a natural granularity that defines sets of data (e.g. a set of database records) that are dependent for the purposes of a given program. The UOW key is selected such that modifications to a record having a certain UOW key value will not affect the program's processing of records having a different UOW key value. Only records sharing UOW key values with modified records will be provided as input to the program when the program runs an update operation. This significantly reduces the number of records that must be processed by the program.

In one embodiment, a UOW key is referred to as a list of attribute names for columns that are part of the UOW key. Consider a program that simply reorganizes, without aggregation of any type, medical test data taken during the many visits of many subjects to a clinical trial location. A change to data taken during one visit of one subject will have no effect on the program's processing of the data for other subjects or even data for the same subject's other visits. Thus, a UOW key of subject-visit may be chosen for the program, meaning that only records that share the same subject-visit column values with any modified record will be provided to the program when the program runs an update operation. Note that a UOW key of subject would also provide correct program results, however more records would input to the program with no impact on the program's results. In general, UOW key having the smallest granularity (e.g., more columns) should be specified for a program to minimize the amount of data that is processed by the program.

For the purposes of updating results of the program, changes in source data are detected and used to identify the distinct set of UOW keys affected. When changes are made to one or more records in the source data, a self-contained set of records having a common UOW key value with respect to the changed records are provided to the program to update the program's results. In this manner, a small subset of records can be provided to the program while ensuring the accuracy of the program's results. The systems and method described herein may operate in a manner that is transparent to the program, so that the program does not require modification to benefit from unit of work based incremental data processing.

The systems and methods of the present description will often be described in the context of a clinical trial for the sake of simplicity and consistency. However, the systems and methods described herein are applicable in any context in which a UOW can be identified with respect to a program that periodically processes source data that is extensive and only a small subset of the source data changes at any given time. For example, the systems and methods described herein have applicability in systems like data warehouses or frameworks for automating execution of user-defined programs (including custom and generated programs) where the system employing the UOW approach runs programs that are not predefined as part of a static system, but must be incorporated to implement client-defined processing flows.

Use of a UOW driven approach can be generalized into two steps. First, the UOW key values of any source records that have been modified are identified. Various techniques for identifying UOW key values for modified source records are described in more detail below and include accessing source table timestamp information to populate a table listing UOW key values for modified source records, or accessing source tracking tables that are populated by a database handling the source tables to identify UOW key values for modified source records. Second, the records that are provided to the program are filtered to include only those source records that share a common UOW key value with a modified source record. One technique, described below, for filtering the source records input to the program is by generating a view of source tables that is input to the program that includes appropriate filter criteria. Other techniques may be employed, such as querying the source tables for records having the UOW key values and providing the results of the query to the program.

With reference to FIG. 1, one example embodiment of a system 100 that performs UOW based incremental processing is illustrated. In FIGS. 1-2E control flow, which includes the exchange of information such as UOW key values, is shown by dashed arrows. The flow of records from source data to a program and output by the program is shown by heavy arrows. FIG. 1 shows a single source table and source view, but in many instances several source tables will exist and several source views will be consumed by the program.

The program has a predefined UOW key, which may be stored in metadata used to define the program. The system 100 includes an incremental processing logic 110 that is configured to i) identify the unique set of UOW key values of any source records that have been modified since a last time the program was run and ii) filter source records provided to the program based on the identified UOW key values. The incremental processing logic 110 identifies a UOW key subset that includes UOW key values for source records that have been modified since a last time the program was run. The incremental processing logic 110 causes a UOW record subset that includes source records having a UOW key value in the UOW key subset to be input to the program. Thus the UOW record subset is the set of all records that share a common unit of work key value with any record that has been modified since the last time the program was executed on the source data. The program processes the UOW record subset to update target data that is the output of the program.

Programs which read from database tables can also be configured to access database views (called source views) having the equivalent structure of the source tables. In one embodiment, the UOW record subset is provided to the program by constraining the source views so that only members of the UOW record subset are included in the source views. The source view is initially set up by the incremental processing logic 110 so that it will filter the source records in the source table based on the UOW key subset to include only members of the UOW record subset. In this manner, the incremental processing logic 110 can provide the UOW record subset in a manner that is transparent to the program.

The UOW key for the program is selected such that programmatic transformations performed by the program are self-consistent within the unit of work. The UOW key for a given program should be defined to reflect the structure of the source data and the operation of the program in producing its target data. Selection of a UOW key for a program requires knowledge of the function of the program regarding the interaction of the program's processing within and across units of work. The data within an identified UOW key may have no interaction across records at all—meaning that each source record impacts only one target record at one extreme—or at the other extreme, within a UOW key every source record could impact every target record. However, no source record having a given UOW key value can impact a target record having a different UOW key value.

In one embodiment, selection of the UOW key for a program may be performed manually by a person familiar with the program. In other embodiments, selection of the UOW key may be automatic, based on a functional analysis of the operations performed by the program. For example, it may be determined automatically that a program is simply transformational on a per record basis because operations performed by the program are limited to re-ordering the columns or re-formatting the data in the columns to a preferred format. For such record transformational programs, a UOW of the unique record identifier could be automatically selected. If operations are discovered in the program such as aggregation functions that act on more than one record to produce a target record, a UOW key that captures the dependencies caused by the aggregation functions could be automatically selected.

A goal is to select a finest-grained UOW such that a minimal number of records can be provided to the program while ensuring that interactions are only within the UOW. In the average blood pressure example from above, if the program averages blood pressure across all visits for a given subject, a UOW of subject-visit would not be appropriate because in its calculations, the program uses blood pressure values for all visits for a given subject. If the input to the program was restricted to just a visit in which blood pressure changed, the program would provide an erroneous result. And conversely, if the average blood pressure was averaged only across a single visit, using a UOW of subject would result in reprocessing more records than necessary.

The UOW key for a can be associated with the program, or the program's target table, for use in incrementally updating the program results. In the case of clinical trial data, subject and subject-visit are natural units of work. This is because for many purposes the data processed by programs in this context only impact the particular subject or the particular subject in a particular visit. Almost all clinical trial data uses subject and visit attributes. Over the course of a clinical trial it is common for a subject or, especially, a subject-visit to be complete and unchanging over a much shorter interval than the course of the clinical trial as a whole. In one embodiment rather than source tables, the source data is comprised of files having multiple fields. In this embodiment, the UOW key is one or more field values, rather than columns in a source table.

Figure 2A:
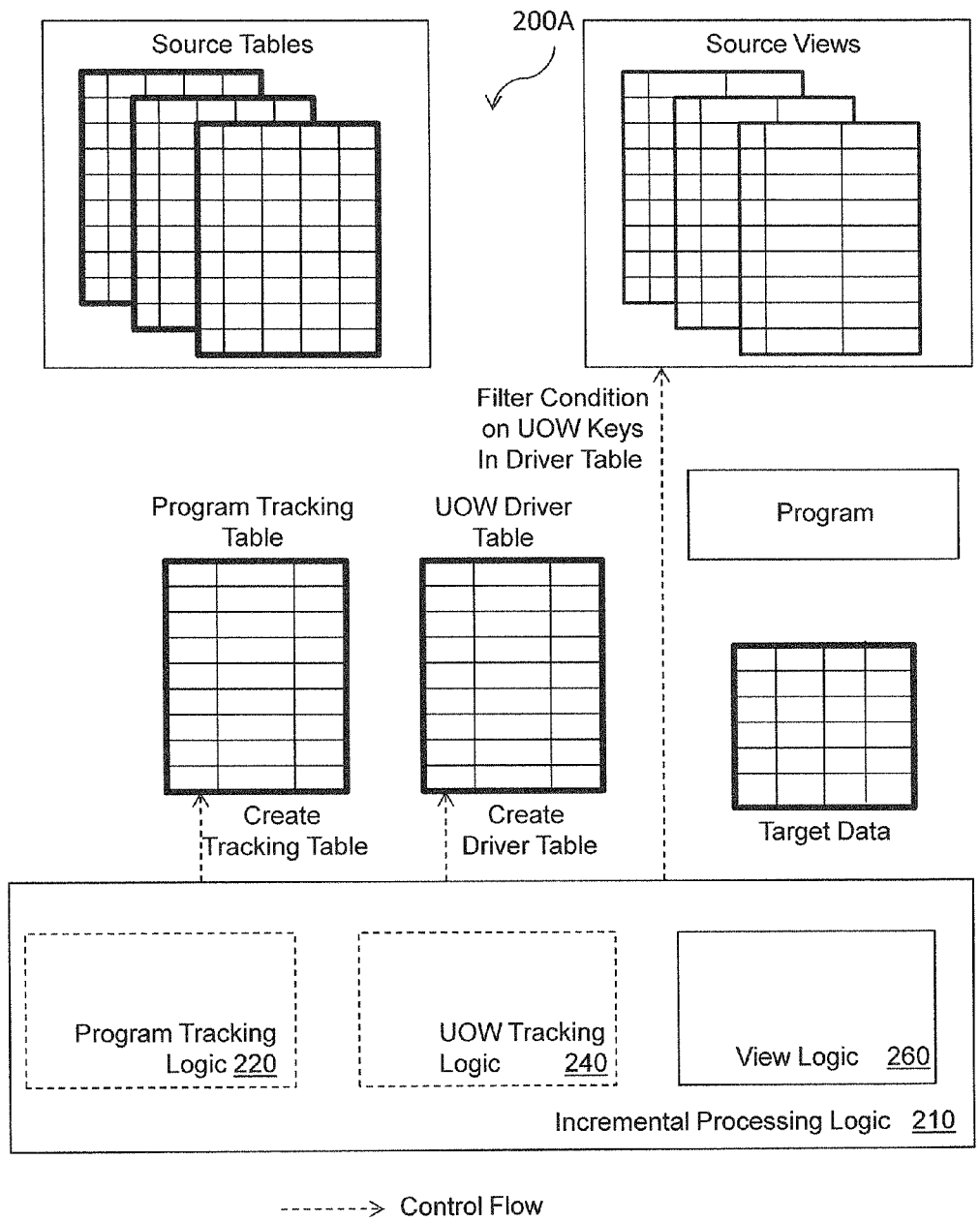
FIGS. 2A-2E illustrate other embodiments of a system associated with unit of work based incremental data processing.

FIG. 2A illustrates one example embodiment of a system 200A that performs unit of work based incremental data processing. FIG. 2A depicts the system 200A in an initial set up phase prior to a program being executed. The system 200A includes an incremental processing logic 210 that is configured to filter, by way of source views, the records that are input to a program. The source views are generated such that the source views select the UOW record subset from the source tables. In this manner, all records that share a common UOW key value with any modified record, across all source tables, are selected by the views and provided to the program.

The incremental processing logic 210 includes a program tracking logic 220, a UOW tracking logic 240, and a view logic 260. The incremental processing logic 210 creates a program tracking table and a UOW driver table. The program tracking logic 220 uses the program tracking table, which is configured to record, in the form of a timestamp or other sequential identifier, the last time the program began execution. The program tracking table will be updated each time the program is executed. In one embodiment, the program tracking table is not explicitly created by the incremental processing logic 210, but rather an existing program tracking mechanism is referred to by the program tracking logic 220.

The UOW tracking logic 240 uses the UOW driver table, which is configured to store UOW key values in the UOW key subset. Thus, the incremental processing logic 210 creates the UOW driver table to include the appropriate number of columns (e.g., one column if UOW key is subject or two columns if UOW key is subject-visit).

The view logic 260 is configured to create views of the source tables that select the UOW record subset. The program will access the source views as input data. The view logic 260 generates source views that access the UOW driver table to filter source records based on the UOW key values stored in the table. In one embodiment, the view logic 260 creates a source view query predicate for each source table that selects records from the source table that have the unit of work key values in the UOW driver table. In this manner, only the UOW record subset (e.g., those records having a common UOW key value with a modified record) will be processed by the program.

In one embodiment, rather than recording UOW key values in the UOW driver table and creating views that access the UOW driver table, the views may be created to access the source tables directly. This direct access approach may be fairly efficient if indexes exist on UOW keys and timestamp values. The view may be created to select records with timestamps after the last program execution and all other records sharing a common UOW with those records. Thus, a view query may be executed on the data source that selects all records having a unit of work key in common with any record that has been created, modified, or deleted since a last time the program was executed.

Figure 2B:
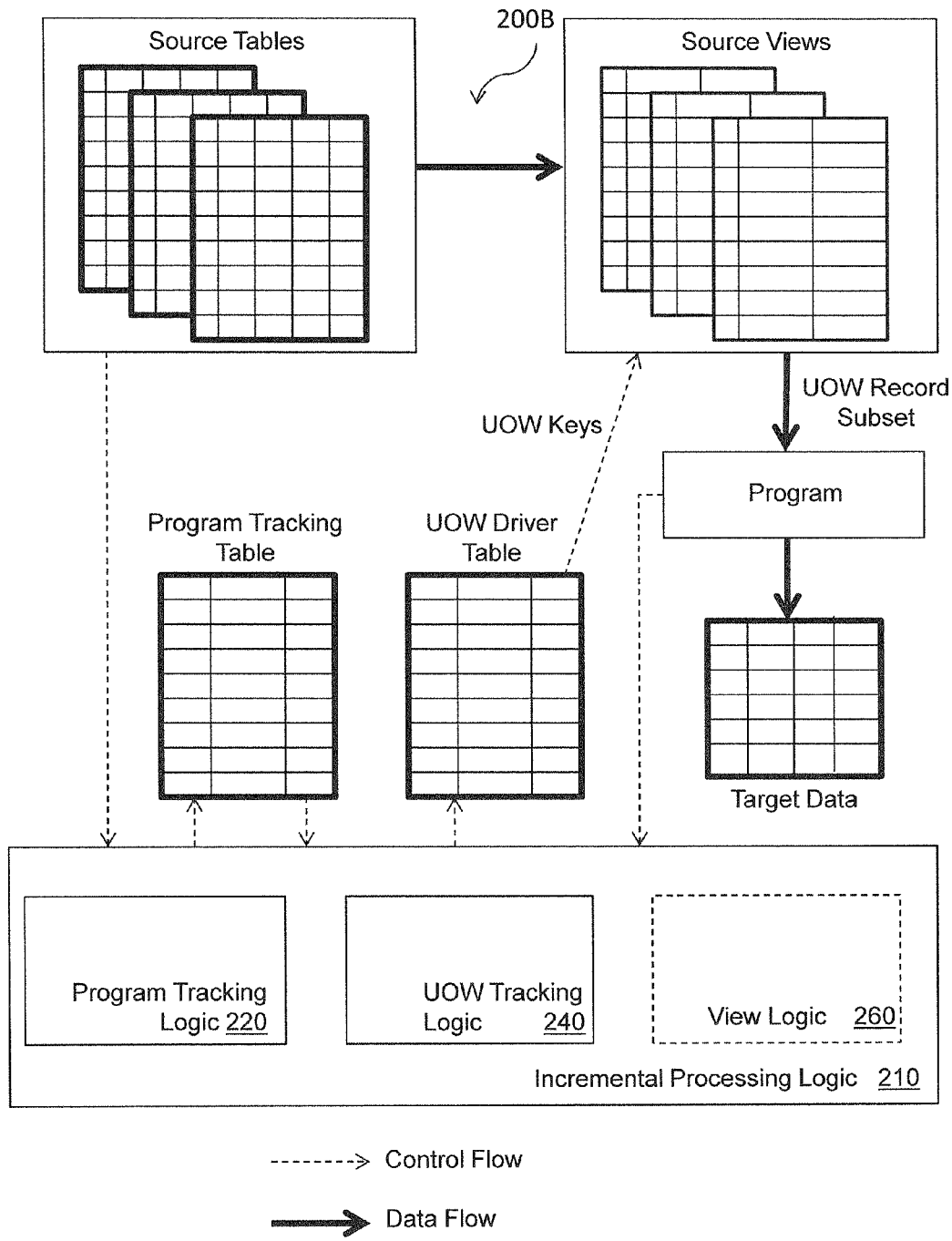

FIG. 2B depicts a system 200B during program execution. The program tracking logic 210 is configured to store in the program tracking table, after each program execution, a timestamp that records the time the program began execution. The UOW tracking logic 240 is configured to identify the UOW key subset when the program is called upon to update its target data. To accomplish this, the UOW tracking logic 240 first identifies records in all source tables that have been modified since a last time the program was run. The UOW tracking logic 240 accesses the program tracking table to determine the time when the last time the program was executed. The UOW tracking logic 240 then identifies as modified all records in any source table that have been modified since the time recorded in the program tracking table.

For each modified record, the UOW tracking logic 240 records a UOW key value in the UOW driver table, if the UOW key value is not already recorded in the UOW driver table. For example, if the UOW key for the program is subject, the UOW tracking logic records, in the UOW driver table, the subject of any record in any source table that has been modified since the last time the program was executed. The source views, as generated by the view logic 260, select records from the source tables that have a UOW key value found in the UOW driver table. The program accesses, as its input, source views of the source tables that select the UOW record subset. After the program completes execution, the program tracking logic 220 updates the program tracking table by recording a timestamp that reflects the time the program began execution.

Figure 2C:
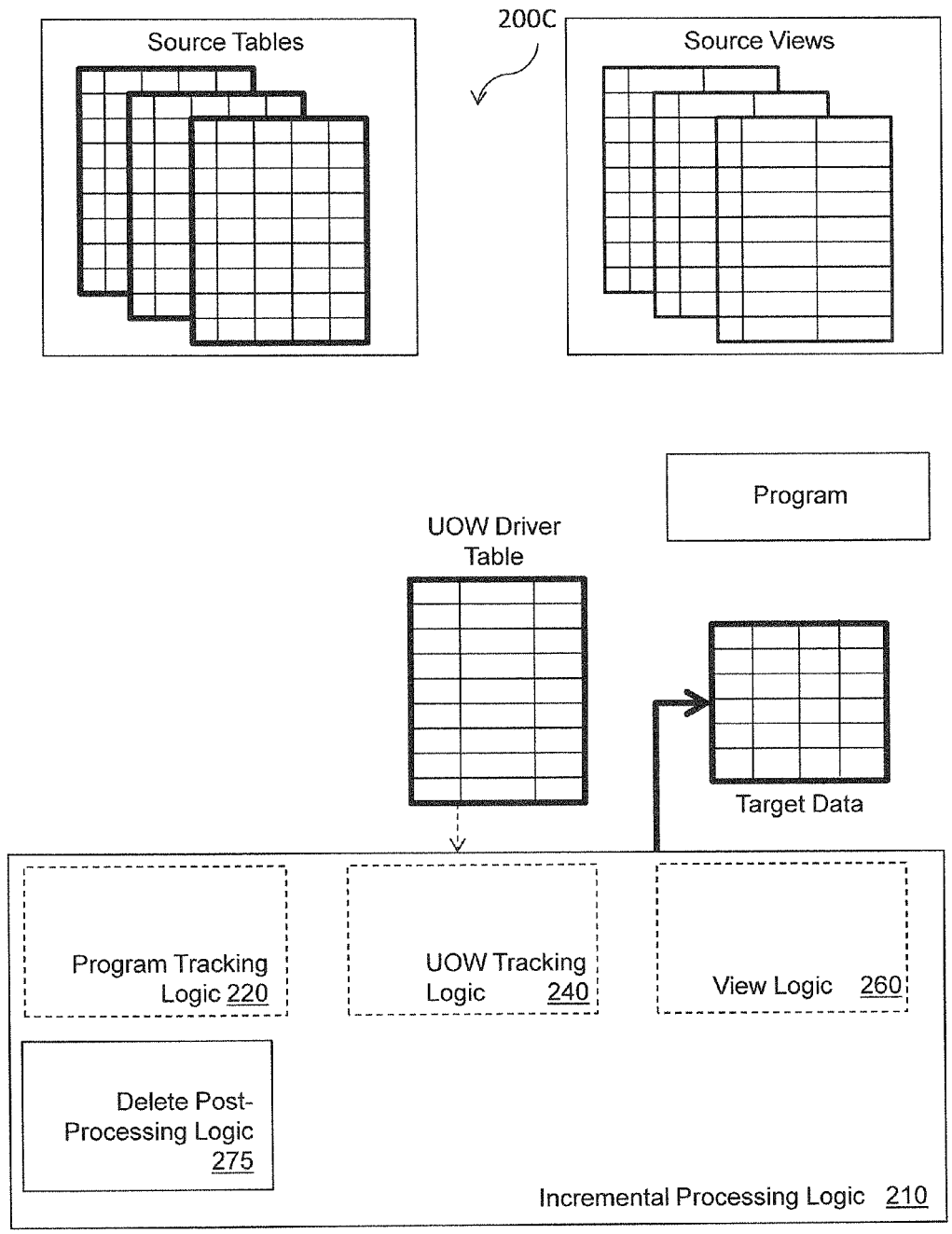

In FIG. 2C, an alternative embodiment of a system 200C is shown that performs UOW based incremental processing. The incremental processing logic 210 includes a delete post processing logic 275. While the delete post processing logic 275 is shown as part of the incremental processing logic 210, the delete post processing logic 275 may be implemented externally with respect to the incremental processing logic to remove newly deleted records from the current target data.

The manner in which deletions in the source tables are propagated to the target data depends on how the target data tables are populated. If the target table is a "reload" type table, records are "managed by insertion." With reload type tables, programs do not explicitly delete records, rather any records that are not "re-inserted" into the table are considered to be deleted and a post processing delete operation removes the deleted records from the table or marks the records as having been deleted using a deletion timestamp or other indicator.

When source views on reload type tables are created, the record having the UOW key value would be marked as deleted and the record would not be selected by the view for input to the program. The source view is created with logic that excludes records that have been marked as deleted from appearing when data is selected from the source view. The delete post-processing logic 275 accesses the UOW driver table to determine the UOWs for all records that were modified since the last program execution, including UOW keys for records that had been marked as deleted in the source table. The delete post-processing logic 275 then analyzes the target data to determine if any record having a UOW key in the UOW driver table has not been modified or refreshed (e.g. written without modification) in the target data table in the last execution of the program. Any record in the target table that has a UOW key value in the UOW driver table that has not been modified or refreshed in the target data table in the just completed execution of the program will be marked as deleted by the delete post-processing logic 275.

For example, if a record is modified in a source table at time B, which is after time A—the last time the program executed, the UOW key value of the record will be recorded in the UOW driver table. However, if the modification of the record having a certain UOW key causes the program to not re-write a record in the target table, the delete post processing logic 275 will detect the (old) target records having the UOW key value and delete them from the target table. Thus, any source record modification that results in one or more records that were previously written to the target table not being written, then the delete post processing will delete the one or more records from the target table.

Figure 3:
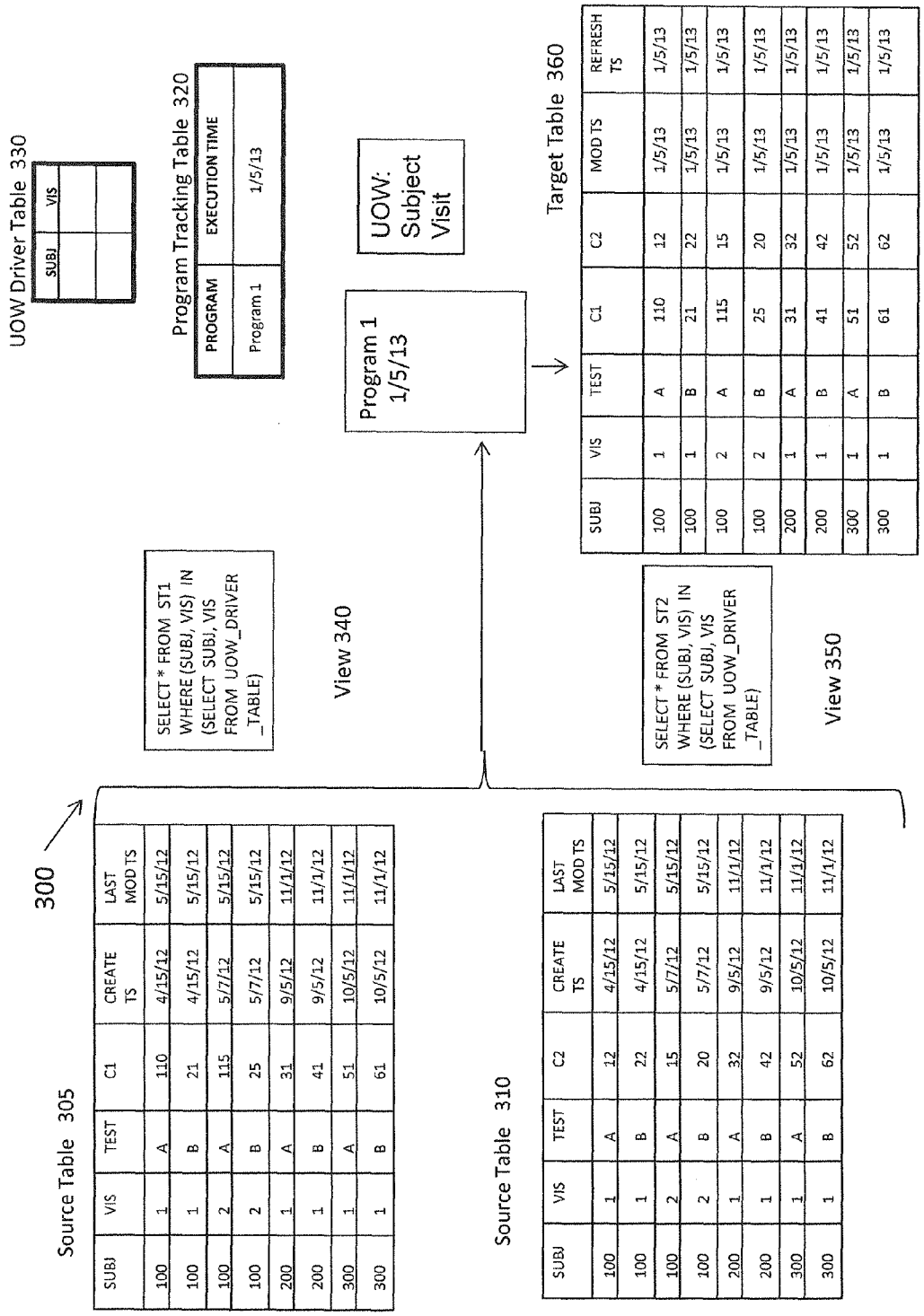
FIGS. 3 and 4 illustrate an example of operation of a system that performs one embodiment of unit of work based incremental data processing.
Figure 4:
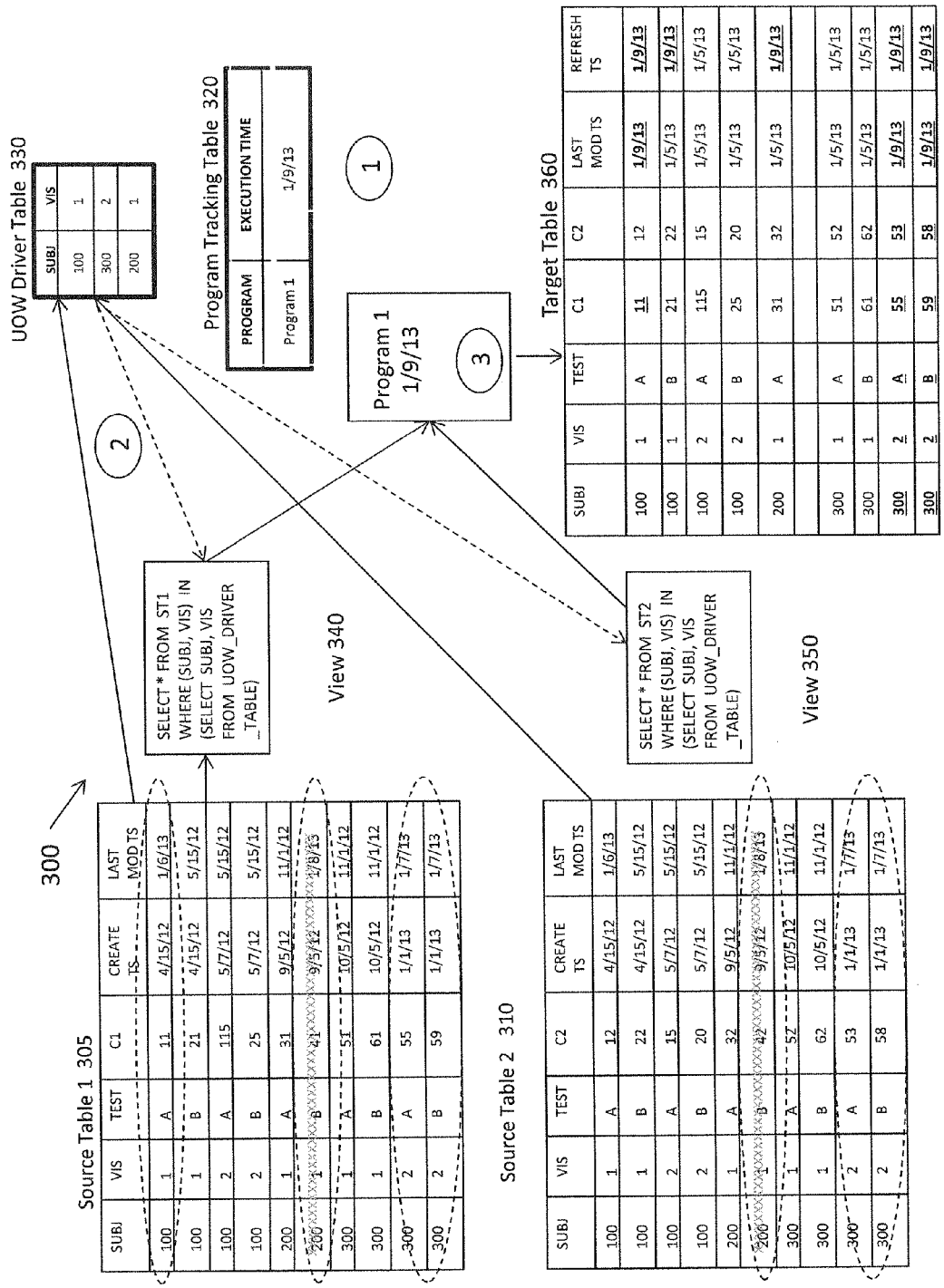

Turning now to FIGS. 3 and 4, an example of how the system of FIGS. 2A-2C may perform UOW based incremental data processing is illustrated. FIG. 3 illustrates the status on Jan. 5, 2013 of several tables just after an initial execution of Program 1. Program 1 processes data from two source tables, 305 and 310. Program 1 has been assigned a UOW key of subject-visit. This UOW key refers to the subject and visit columns of the source tables 305, 310, and of target table 360, as will be described below.

Source table 305 records a result C1 for two tests A and B for each subject at each visit. Source table 305 records data for two visits for subject 100 and one visit for subjects 200 and 300. A creation timestamp column records the creation time of the record (e.g., Apr. 15, 2012 for the record stored in the first row of the table). A last modification timestamp column records the last time the record was modified (e.g., May 15, 2012 for the record stored in the first row of the table). Source table 310 records a result C2 for the two tests A and B for each subject at each visit. Source table 310 records data for two visits for subject 100 and one visit for subjects 200 and 300. For the sake of simplicity, timestamps are at a per day granularity. It is likely that timestamps having a much finer time increment (e.g., seconds) would be used.

Program 1 populates a target table 360 by consolidating the rows in each of the two source tables for each test into a single row. The target table includes a last modification timestamp which records the time at which the particular row was last modified by Program 1. Since the operation performed by Program 1 on Jan. 5, 2013 was a load operation, all of the records in the target table 360 are new records that were inserted (e.g., modified) on Jan. 5, 2013. The target table also includes a refresh timestamp that records the last time a record was written with or without changes by Program 1. Since the operation performed by Program 1 on Jan 5, 2013 was a load operation, all of the records were refreshed on Jan. 5, 2013. In some cases, the last modification timestamp for a row will be different than the refresh timestamp as will be seen in FIG. 4.

A program tracking table 320 records the last time Program 1 was executed. After Program 1 loads the target table 360, the program tracking table 320 shows that Program 1 was last executed on Jan 5,2013. The information in the program tracking table will be used to identify which records in the source tables have been modified since the last time Program 1 was executed.

A UOW driver table 330 is shown that will be used to record UOW key values of modified records the next time Program 1 executes. The UOW driver table 330 is empty in FIG. 3 because the target table 360 has been loaded and the execution time has been recorded. During the Jan 5 2013 execution of Program 1 the UOW driver table contained UOW keys for all records since all records were processed in this initial run.

As part of initial set up for Program 1 a view 340 is created (e.g., by the incremental processing logic 210) that will select records from the source table 305 that have a subject and visit that are in the UOW driver table 330. Thus, the view 340 will include the records in source table 305 that were modified as well as all records in source table 305 that share a common UOW key value with modified source records from either source table.

A view 350 is created (e.g., by the incremental processing logic 210) that will select records from the source table 310 that have a subject and visit that are in the UOW driver table 330. Thus, the view 350 will include the records in source table 310 that were modified as well as all records in source table 310 that share a common UOW key value with the modified source records. Note that because the UOW key is subject-visit, the records that have a common subject value with modified records, but not a common visit value are not selected by the views 340, 350.

Referring now to FIG. 4, Program 1 is performing an incremental update operation on Jan 9 2013. Since the last time Program 1 was run, on Jan. 5, 2013, several changes have been made to the source tables 305, 310. In source table 305 the C1 value for test A has been corrected from 110 to 11 on Jan. 6, 2013. In source tables 305 and 310 the record for subject 200 visit 1, test B was deleted on Jan 8 2013 and data for subject 300 visit 2 was added on Jan. 7, 2013.

To begin UOW based incremental processing, first the program tracking table is accessed to identify the last time Program 1 was executed (e.g., Jan. 5,2013, note that the value in the program tracking table was Jan 5, 2013 at the start of the Jan 9,2013 execution as shown in FIG. 3). To compile the UOW record subset, the source tables are scanned to identify any records that have been modified since the last time Program 1 executed (e.g. since Jan. 5,2013).

The circled record in source table 305 for subject 100 has a source last modification timestamp of Jan 6,2013, which is later than Jan. 5,2013. This record is identified as having been modified. Recall that the UOW key for Program 1 is subject-visit. The UOW key value for the modified record, subject 100 and visit 1, is recorded in the UOW driver table 330. The circled new records in source tables 305 and 310 for subject 300 have a source last modification timestamp of Jan 7,2013, which is later than Jan 5,2013. These records are identified as having been modified. The UOW for the new records, subject 300 and visit 2 is recorded in the UOW driver table 330. The records for subject 200 visit 1 test B were deleted from source tables 305, 310 on Jan 8,2013. The UOW for the deleted records, subject 200 and visit 1, is recorded in the UOW driver table 330.

The view 340 selects records from the source table 305 that have a subject and visit that are in the UOW driver table 330. Thus, the view 340 will filter the records in the source table 305 such that the view 340 will select all records in source table 305 that share a common UOW key value (e.g., subject 100 visit 1, subject 200 visit 1, and subject 300 visit 2) found in the UOW driver table 330. Note that these selected records include all modified records in the table.

The view 350 selects records from the source table 310 that have a subject and visit that are in the UOW driver table 330. Thus, the view 350 will filter the records in the source table 310 such that the view 350 will include all modified records and all records in source table 310 that share a common UOW key value (e.g., subject 100 visit 1, subject 200 visit 1, and subject 300 visit 2) found in the UOW driver table 330. The records for subject 200, visit 1, test B are not selected by either view because they have been deleted from the source tables 305, 310. Note that because the UOW key is subject-visit, the records that have a common subject value with modified records, but not a common visit value are not selected by the views 340, 350.

The views 340, 350 filter the input data for Program 1 to ten records: the two rows for subject 100 visit 1, one row for subject 200 visit 1, and the two rows for subject 300 visit 2 in each of the source tables 305, 310. Program 1 processes just these ten records and updates the target table 360 as shown (modifications are shown in bold and underline in target table 360). The value for C1 in first row of the target table corresponds the modified value of 11 in source table 305. The last modification timestamp and refresh timestamp are set to Jan. 9, 2013, reflecting the time at which Program 1 changed the record. Recall that, due to their UOW key of patient 100 visit 1, the second row of source table 305 was read by Program 1 through the view 340 and the first two rows of the source table 310 were also read by Program 1 through the view 350. To reflect this, the refresh timestamp for the second row of the target table is set to Jan 9, 2013 to indicate that this row was written without changes on Jan. 9,2013. The last two rows of the target table 360 record results of the new records for patient 300 visit 2. The last modification timestamp and refresh timestamp are set to Jan 9,2013, reflecting the time at which Program 1 inserted the records into the target table.

The entire record for subject 200, visit 1, test B is now missing from the target table (or otherwise indicated as deleted). Recall that the rows of the source tables 305, 310 that include values for subject 200 visit 1 were also read by Program 1 through the views 340, 350. The refresh timestamp for the other row of the target table that records subject 200 visit 1 is set to Jan. 9,2013 to indicate that this row was written without changes on Jan 9, 2013.

If all of the data for a target record comes from source records that have been deleted, or if source record modifications cause a record that was previously written to the target table to not be re-written to the target table, then the record in the target table will have a UOW key value found in the UOW driver table, yet will not have been refreshed or modified. The target record's last modification timestamp and refresh timestamp will predate the time of program execution. This will result, possibly using the post processing delete technique described in FIG. 2C, in the entire record being deleted from the target data. After the target table 360 is updated as shown in FIG. 4, the program tracking table 320 is modified to record a time of Jan .9,2013.

Figure 2D:
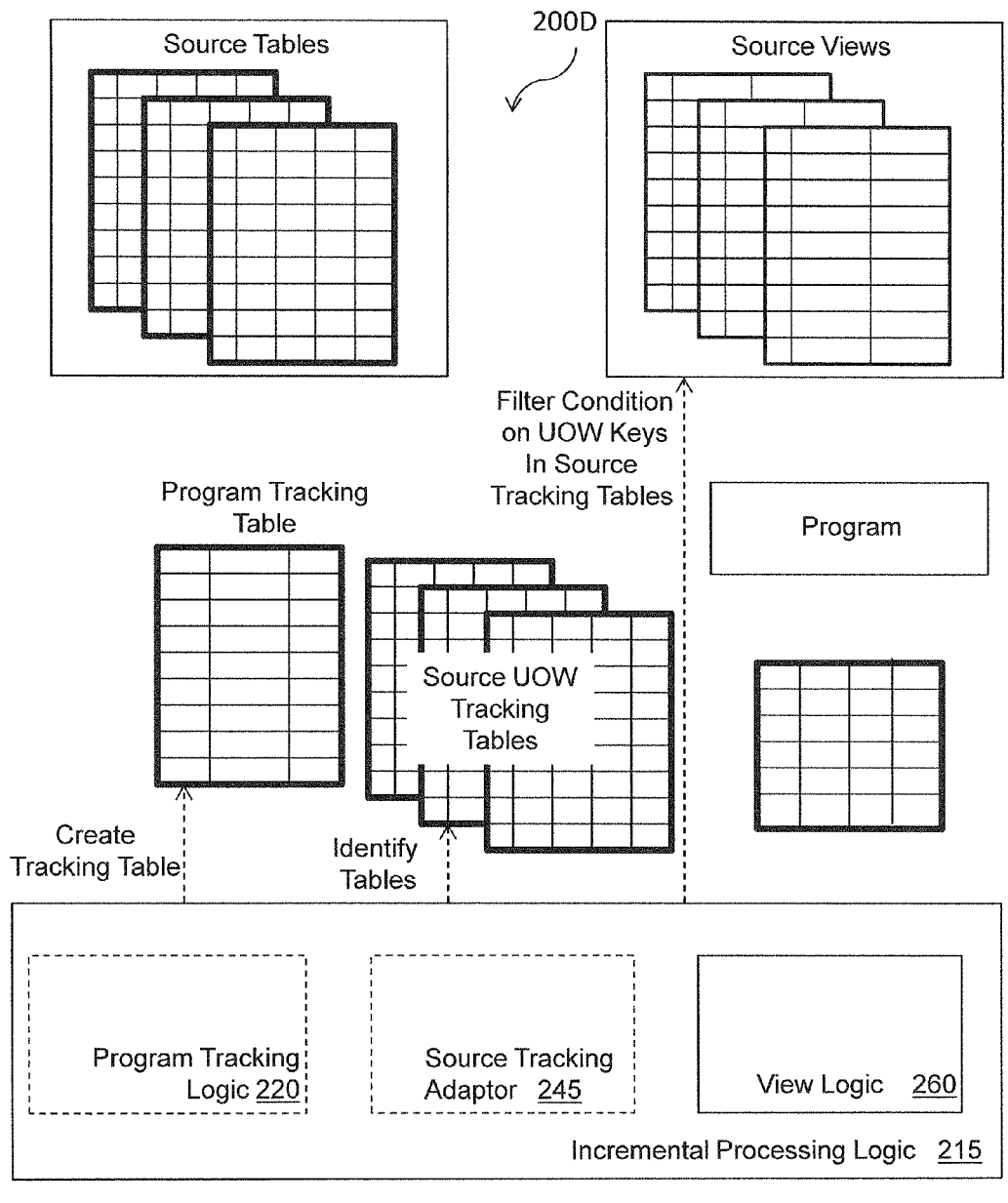
Figure 2E:
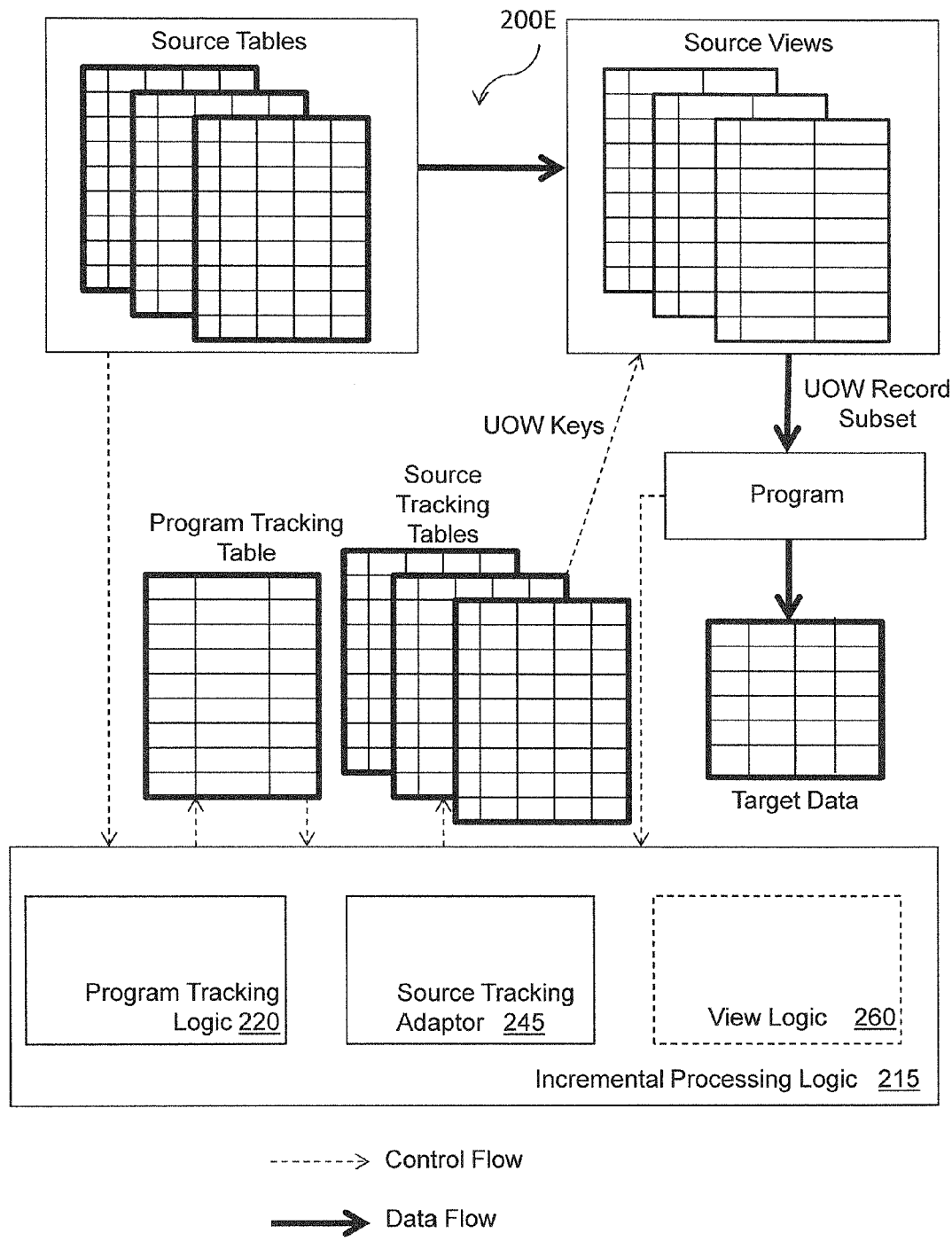

Referring now to FIG. 2D, an alternative embodiment of a system 200D is shown that includes an incremental processing logic 215 that uses an alternative method to detect UOW key values for modified source records. to perform UOW based incremental processing. FIG. 2D depicts the system 200D in an initial set up phase prior to a program being executed. The system 200D includes an incremental processing logic 215 that is configured to filter, by way of source views, the records that are input to a program. The source views are generated such that the source views select the UOW record subset from the source tables. In this manner, all records that share a common UOW key value with any modified record, across all source tables, are selected by the views and provided to the program.

The incremental processing logic 215 includes a program tracking logic 220, a source tracking adaptor 245, and a view logic 260. The incremental processing logic 215 creates a program tracking table configured to record, in the form of a timestamp or other sequential identifier, the last time the program began execution. The program tracking table will be updated each time the program is executed. The incremental processing logic 215 identifies source UOW tracking tables that are associated with the source tables. The source UOW tracking tables record, for each UOW key value, a last modification date for any record having that UOW key value.

The view logic 260 is configured to create views of the source tables that select the UOW record subset from the source UOW tracking tables identified by the source tracking adaptor. The program will access the source views as input data. The view logic 260 generates source views that access the source UOW tracking tables to filter source records based on the UOW key values stored in the table. In one embodiment, the view logic 260 creates a source view query predicate for each source table that selects records from the source table that have the unit of work key values in any of the source UOW tracking tables indicated as having been modified since a last time the program executed. In this manner, only the UOW record subset (e.g., those records having a common UOW key value with a modified record) will be processed by the program. An example view query for a system with two source UOW tracking tables Source Tracking T1 and Source Tracking T2 that selects records that have been modified since Jun. 1,2013 follows:

SELECT * FROM ST1 WHERE (SUB,VIS) IN
(SELECT SUBJ, VIS
FROM SOURCE_TRACKING_T1
WHERE LAST_UPDATE>Jun. 1,2013
UNION
SELECT SUBJ, VIS
FROM SOURCE_TRACKING_T2
WHERE LAST_UPDATE>Jun. 1,2013
This view query can be compared with the view queries seen in FIGS. 3 and 4 that access the UOW driver table instead of source UOW tracking tables.

FIG. 2E depicts a system 200E during program execution. The source tracking adaptor 245 accesses information maintained about the source tables to identify UOW key values for modified source records. The source tracking adaptor 245 is configured to interact with a data management system that handles the source tables to maintain a source tracking table. In one embodiment, the source tracking adaptor 245 maintains, for each source table, a source tracking table that includes a single record for each unique UOW key value and records the most recent time any record having the UOW key value has been modified. The source tracking adaptor 245 may incorporate database triggers or other tracking mechanism associated with the database system that handles the source tables.

The view logic 260 functions in a similar manner as described above with respect to FIG. 2A to generate source views that access the source tracking tables (rather than a UOW driver table) to select records in the UOW record subset. Thus, by using the source tracking adaptor 245, the preprocessing that is performed by the UOW tracking logic 240 to populate a UOW driver table is avoided. The views are generated so that they access the source tracking tables to filter the source tables for input to the program. While the source tracking adaptor 245 is shown as part of the incremental processing logic 215, source tracking adaptor 245 may be implemented externally with respect to the incremental processing logic to populate the source UOW tracking tables.

Figure 5:
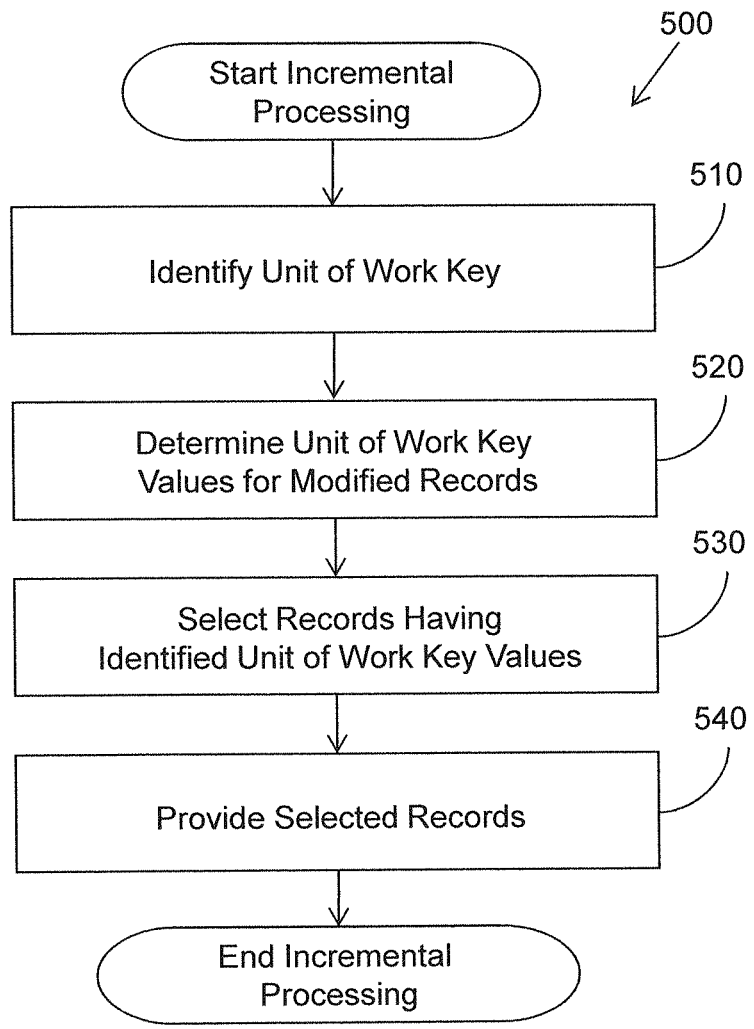
FIG. 5 illustrates an embodiment of a method associated with unit of work based incremental data processing.

Referring now to FIG. 5, one example embodiment of a method 500 for performing unit of work based incremental processing is shown. The method 500 may be performed by the incremental processing logics 110, 210, or 215 of FIGS. 1 and 2. The method includes, at 510, identifying a UOW key associated with a program. The UOW key for a program is determined a priori as described above and mapped to the program or the program's target table, possibly as part of metadata for the program or target table. At 520, the method includes determining respective unit of work key values for respective records in the data source or sources that have been modified (e.g., inserted, updated, deleted) since a last time the program was executed. At 530, a set of records is selected from the data source that have the identified unit of work key values. At 540, the selected set of records is provided to the program. In the described embodiments, the selected set of records is provided by way of a view on each source table that selects only records with the UOW key values. In this manner, records in the data source that do not have the identified unit of work key values are not provided to the program, reducing the amount of processing that is performed by the program to update its results to reflect modified source data.

Figure 6:
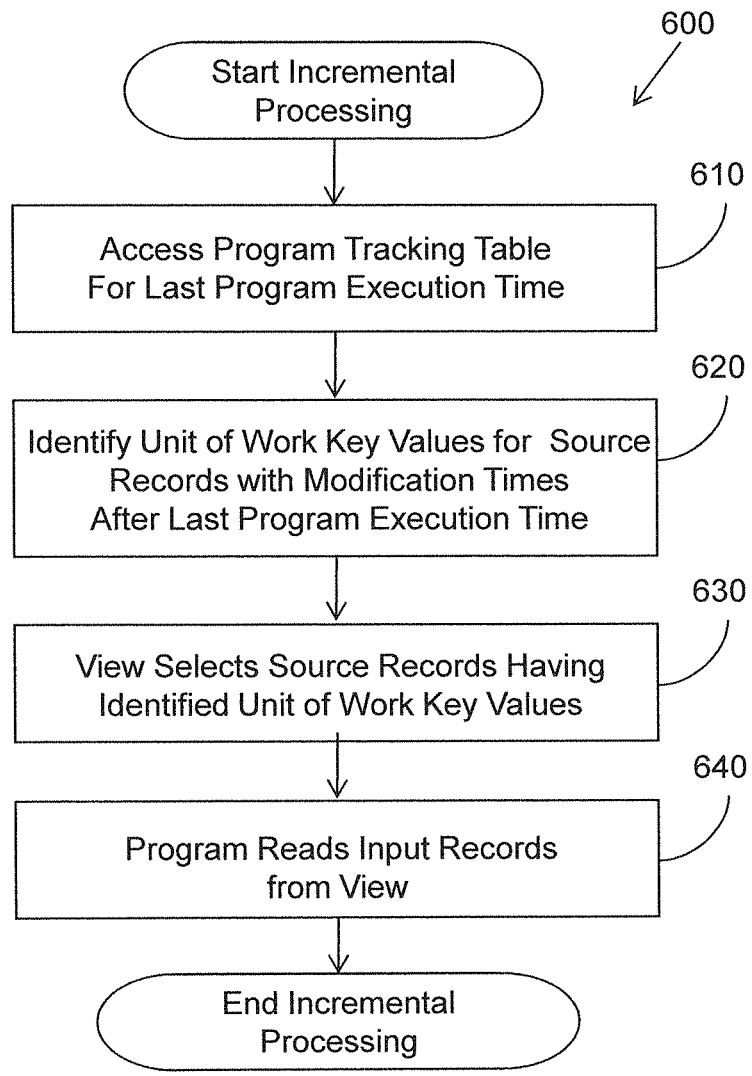
FIG. 6 illustrates another embodiment of a method associated with unit of work based incremental data processing.

FIG. 6 illustrates one example embodiment of a method 600 that enables incremental processing for a program that processes data from a data source. The method includes, at 610, accessing a program tracking table that includes a record of a timestamp for when the program was last executed. At 620, the method includes identifying respective UOW key values for respective records in the data source having a last modification time that is later than the time of the last program execution. A UOW driver table is populated with UOW key values for records that have been modified since the last time the program was executed.

At 630, a view of each source table selects a set of records from the source table that have a UOW key value in the UOW driver table. The view may be created by constructing a view query that selects, for the view, records from the source table that have the unit of work key values in the unit of work driver table. At 640 the program reads input records from the view. In this manner the program inputs records in the UOW record subset from the source tables as filtered by the views.

Figure 7:
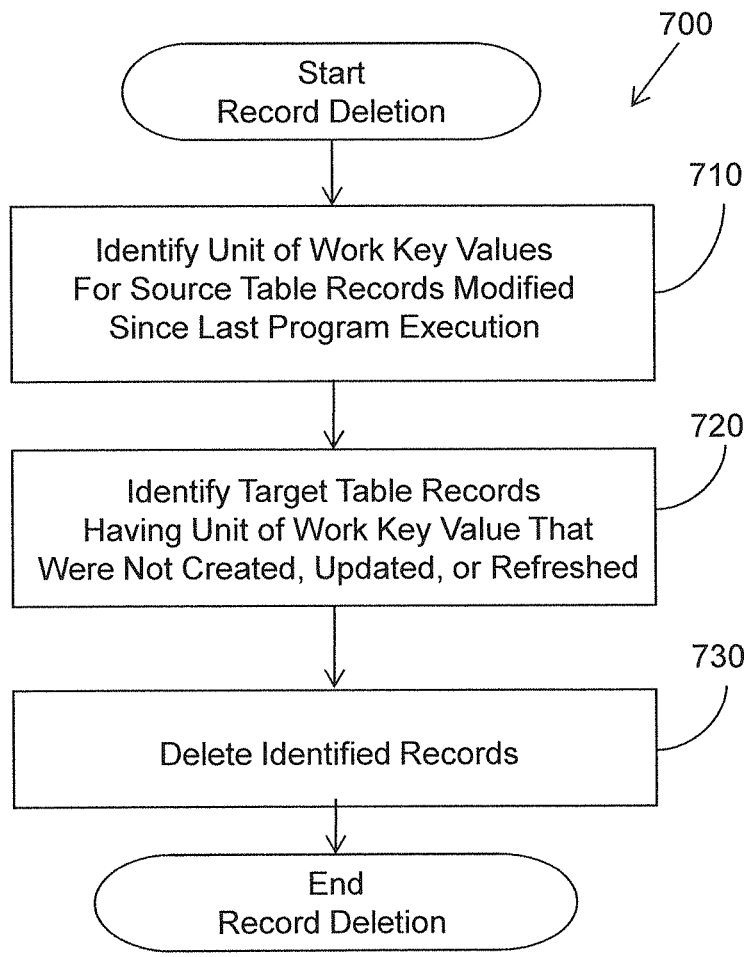
FIG. 7 illustrates another embodiment of a method associated with unit of work based incremental data processing.

FIG. 7 illustrates one example embodiment of a method 600 that deletes records from a target table after incremental processing has been performed by a program as described above. The method 700 may be performed by delete post-processing logic 275 of FIG. 2C. The method includes, at 710, identifying UOW key values for source records that have been modified since a last time the program was executed. At 720, the method includes identifying records having the UOW key values in the target table that were not created, updated, or refreshed in the last program execution. At 730, the method includes deleting the identified records from the target table.

While the same UOW key has been used for all source tables accessed by the program in many foregoing examples, a program can read from several data sources with different, overlapping keys. There are several approaches to selecting UOW keys when source tables have different keys. A UOW selection logic is configured to select working UOW keys for each source table based on available keys in each respective source table. While the UOW key for a program does not change, working UOW keys can change depending on the keys in the source tables and possibly the nature of changes made to the source tables. The source views will select records in each source table based on the working UOW keys selected by the UOW key selection logic.

A first approach is to deprecate to the shortest UOW key amongst the source tables. The UOW selection logic selects a working UOW key to be used for all source views by deprecating to the shortest common key among all the source tables. For example, if a program is self-consistent within Subject-Visit, the program's longest possible UOW key is Subject-Visit. If a first source table has a Subject key (e.g., does not have a Visit column), while a second source table has a Subject-Visit key, the UOW selection logic would select a working UOW key of Subject for the source views on both the first source table and the second source table.

Alternatively, there are cases where a longer UOW key for the target can be used and the UOW selection logic 820 can determine the actual UOW processing to carry out. For instance, the UOW selection logic could determine only the Subject-Visit table has data changes and use this information to determine that the working UOW key for the source view on the Subject-Visit table can use the Subject-Visit key UOW. A working UOW key of Subject can be used for the source view on the Subject table to select the Subjects for these changed Subject-Visits.

Figure 8:
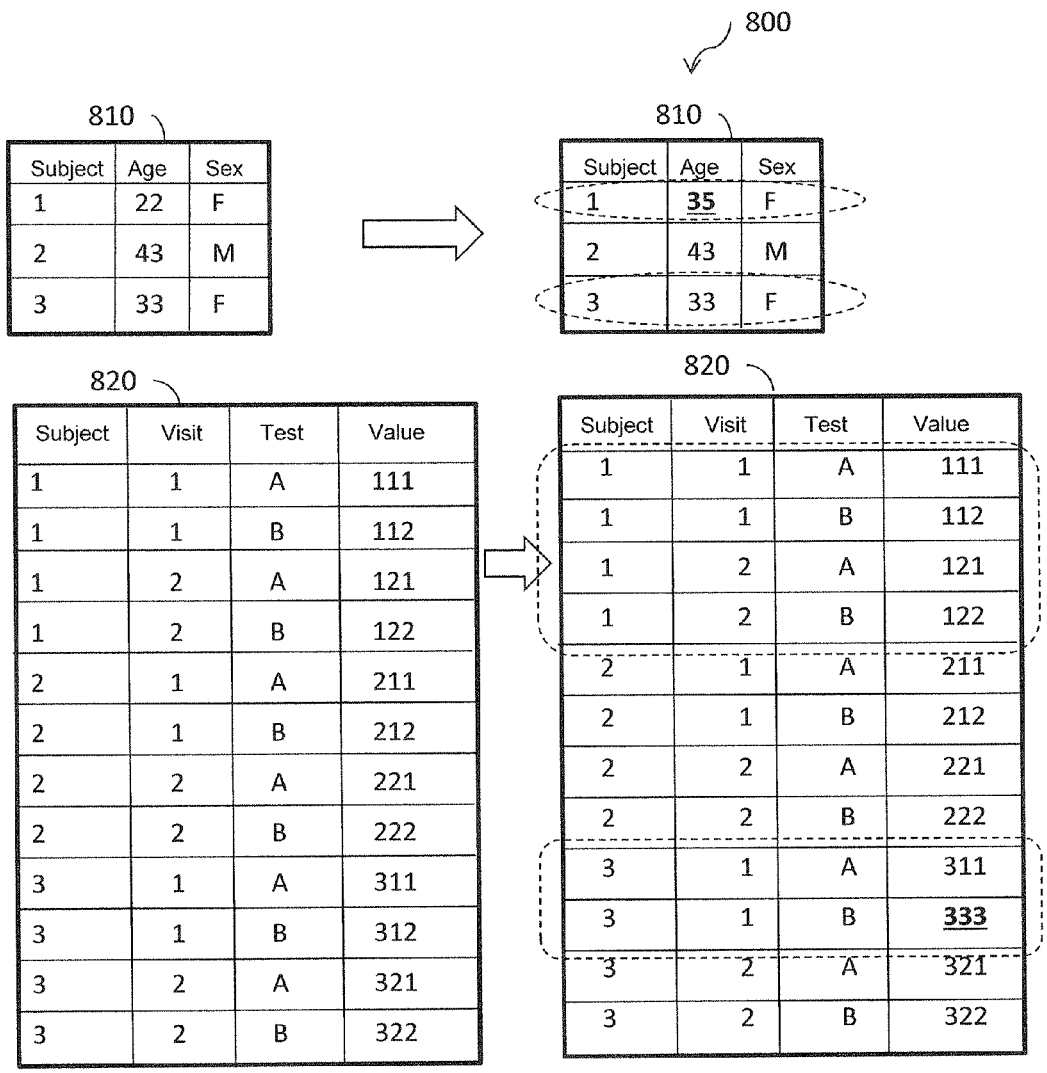
FIG. 8 illustrates one embodiment of a system associated with unit of work based incremental data processing.

FIG. 8 illustrates an example technique for performing an even more efficient approach to selecting UOW keys. In FIG. 8 a Subject source table 810 and a Subject-Visit source table 820 have been changed as shown (changes in bold and underline). For the Subject table 810 with Subject UOW changes, the UOW selection logic includes 1) those records (e.g., subject 1) and the UOW selection logic also includes 2) all Subject-Visit records for those subjects from Subject-Visit sources (e.g., subject 1, visit 1 and subject 1, visit 2). For the Subject-Visit table 820 with Subject-Visit UOW changes, the UOW selection logic includes 3) only those Subject-Visit records with changes (unless already included by Subject table change)(e.g., subject 3, visit 1) and the UOW selection logic also includes 4) all subject records for the subject key portion of the changed Subject-Visit records from the Subject table changes (unless already included by Subject table change)(e.g., subject 3).

As can be seen from the foregoing description, in unit of work based incremental data processing an appropriate unit of work key is selected for a program that processes source data that is subject to modification. The unit of work key is selected such that modifications to a record having a certain unit of work key value will not affect the program's processing of records having a different unit of work key value. When the program updates its target data, rather than re-processing all the source data, only those records that share a common unit of work key value with records that have been modified since a last time the program was executed are provided to the program. The program does not need to be modified to process the selected subset of records, making the methods and systems described herein easy to implement in many different environments. In this manner, a much smaller set of data can be processed by the program while the accuracy of the program's target data is maintained.

General Computer Embodiment

Figure 9:
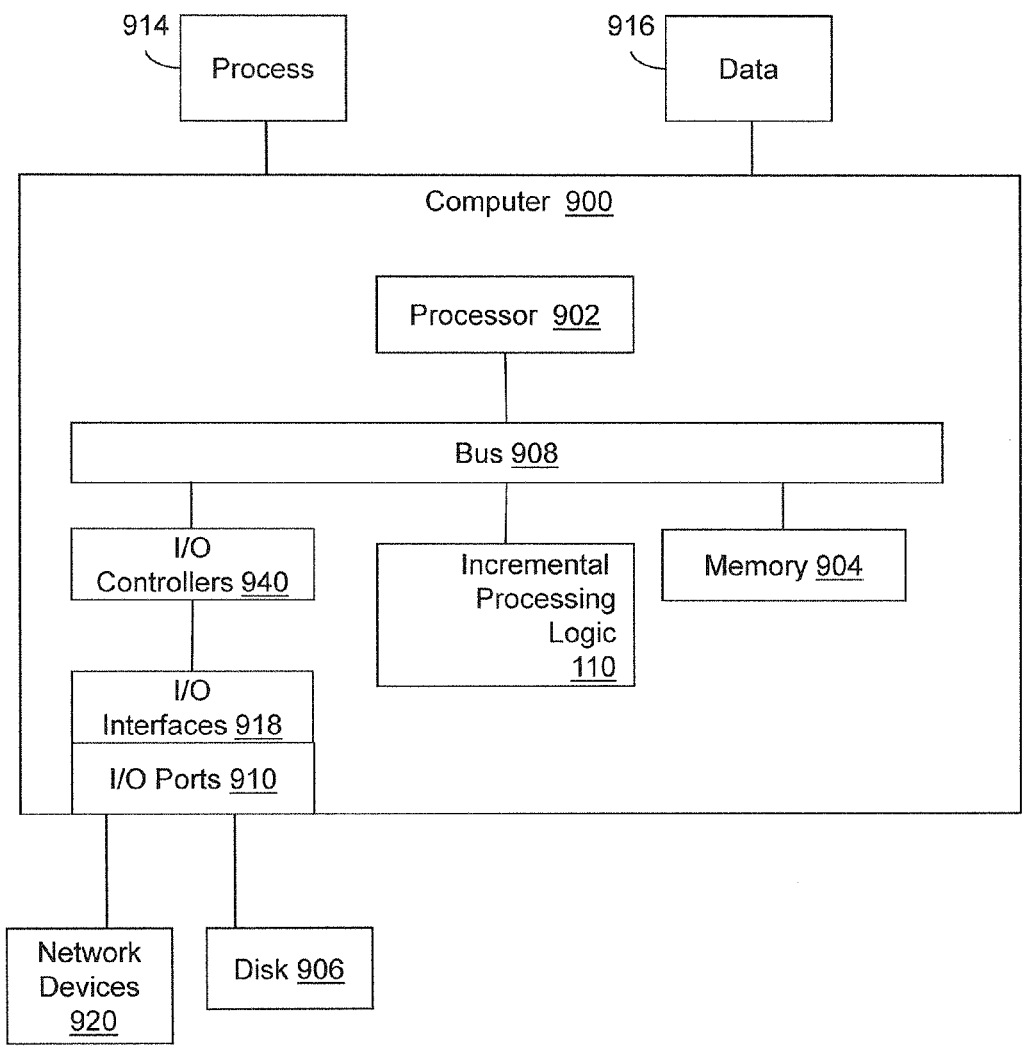
FIG. 9 illustrates an embodiment of a computing system in which example systems and methods, and equivalents, may operate.

FIG. 9 illustrates an example computing device in which example systems and methods described herein, and equivalents, may operate. The example computing device may be a computer 900 that includes a processor 902, a memory 904, and input/output ports 910 operably connected by a bus 908. In one example, the computer 900 may include an incremental processing logic 930 configured to facilitate unit of work based incremental data processing. In different examples, the incremental processing logic 930 may be implemented in hardware, a non-transitory computer-readable medium with stored instructions, firmware, and/or combinations thereof. While the incremental processing logic 930 is illustrated as a hardware component attached to the bus 908, it is to be appreciated that in one example, the incremental processing logic 930 could be implemented in the processor 902.

In one embodiment, incremental processing logic 930 is a means (e.g., hardware, non-transitory computer-readable medium, firmware) for performing unit of work based incremental data processing. The instructions include selecting a unit of work key for a program that processes records in a source table. The unit of work key is selected such that modifications to a record having a certain unit of work key value will not affect the program's processing of records having a different unit of work key value. The instructions include associating the selected unit of work key with the program; and when a record in the source table is modified, identifying a unit of work key value for the record. A selected set of records having the identified unit of work key value is provided to the program. In this manner, records in the data source that do not have the identified unit of work key values are not provided to the program.

The means may be implemented, for example, as an ASIC programmed to perform unit of work based incremental data processing. The means may also be implemented as stored computer executable instructions that are presented to computer 900 as data 916 that are temporarily stored in memory 904 and then executed by processor 902.

Incremental processing logic 930 may also provide means (e.g., hardware, non-transitory computer-readable medium that stores executable instructions, firmware) for performing unit of work based incremental data processing.

Generally describing an example configuration of the computer 900, the processor 902 may be a variety of various processors including dual microprocessor and other multiprocessor architectures. A memory 904 may include volatile memory and/or non-volatile memory. Non-volatile memory may include, for example, ROM, PROM, and so on. Volatile memory may include, for example, RAM, SRAM, DRAM, and so on.

A disk 906 may be operably connected to the computer 900 via, for example, an input/output interface (e.g., card, device) 918 and an input/output port 910. The disk 906 may be, for example, a magnetic disk drive, a solid state disk drive, a floppy disk drive, a tape drive, a Zip drive, a flash memory card, a memory stick, and so on. Furthermore, the disk 906 may be a CD-ROM drive, a CD-R drive, a CD-RW drive, a DVD ROM, and so on. The memory 904 can store a process 914 and/or a data 916, for example. The disk 906 and/or the memory 904 can store an operating system that controls and allocates resources of the computer 900.

The bus 908 may be a single internal bus interconnect architecture and/or other bus or mesh architectures. While a single bus is illustrated, it is to be appreciated that the computer 900 may communicate with various devices, logics, and peripherals using other busses (e.g., PCIE, 1394, USB, Ethernet). The bus 908 can be types including, for example, a memory bus, a memory controller, a peripheral bus, an external bus, a crossbar switch, and/or a local bus.

The computer 900 may interact with input/output devices via the i/o interfaces 918 and the input/output ports 910. Input/output devices may be, for example, a keyboard, a microphone, a pointing and selection device, cameras, video cards, displays, the disk 906, the network devices 920, and so on. The input/output ports 910 may include, for example, serial ports, parallel ports, and USB ports.

The computer 900 can operate in a network environment and thus may be connected to the network devices 920 via the i/o interfaces 918, and/or the i/o ports 910. Through the network devices 920, the computer 900 may interact with a network. Through the network, the computer 900 may be logically connected to remote computers. Networks with which the computer 900 may interact include, but are not limited to, a LAN, a WAN, and other networks.

In another embodiment, the described methods and/or their equivalents may be implemented with computer executable instructions. Thus, in one embodiment, a non-transitory computer-readable medium is configured with stored computer executable instructions that when executed by a machine (e.g., processor, computer, and so on) cause the machine (and/or associated components) to perform the methods described in FIGS. 1-9.

While for purposes of simplicity of explanation, the illustrated methodologies in the figures are shown and described as a series of blocks, it is to be appreciated that the methodologies are not limited by the order of the blocks, as some blocks can occur in different orders and/or concurrently with other blocks from that shown and described. Moreover, less than all the illustrated blocks may be used to implement an example methodology. Blocks may be combined or separated into multiple components. Furthermore, additional and/or alternative methodologies can employ additional blocks that are not illustrated.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

ASIC: application specific integrated circuit.
CD: compact disk.
CD-R: CD recordable.
CD-RW: CD rewriteable.
DVD: digital versatile disk and/or digital video disk.
HTTP: hypertext transfer protocol.
LAN: local area network.
PCI: peripheral component interconnect.
PCIE: PCI express.
RAM: random access memory.
DRAM: dynamic RAM.
SRAM: synchronous RAM.
ROM: read only memory.
PROM: programmable ROM.
EPROM: erasable PROM.
EEPROM: electrically erasable PROM.
SQL: structured query language.
OQL: object query language.
USB: universal serial bus.
WAN: wide area network.

"Computer-readable medium", as used herein, refers to a non-transitory medium that stores instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read. The definition of computer-readable medium is hereby specifically limited to include only subject matter which is statutory under 35 U.S.C §101.

"Computer storage medium", as used herein, is a non-transitory medium that stores instructions and/or data. Computer storage medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of computer storage medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read. Computer storage medium described herein are limited to statutory subject matter under 35 U.S.C §101.

"Logic", as used herein, includes a computer or electrical hardware component(s), firmware, a non-transitory computer readable medium that stores instructions, and/or combinations of these components configured to perform a function(s) or an action(s), and/or to cause a function or action from another logic, method, and/or system. Logic may include a microprocessor controlled by an algorithm, a discrete logic (e.g., ASIC), an analog circuit, a digital circuit, a programmed logic device, a memory device containing instructions that when executed perform an algorithm, and so on. Logic may include one or more gates, combinations of gates, or other circuit components. Where multiple logics are described, it may be possible to incorporate the multiple logics into one physical logic component. Similarly, where a single logic unit is described, it may be possible to distribute that single logic unit between multiple physical logic components. The definition of logic is hereby specifically limited to include only subject matter which is statutory under 35 U.S.C §101.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the disclosure is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

No claim is intended to cover non-statutory subject matter under §101 and shall not be construed to be non-statutory under §101.

To the extent that the term "or" is used in the detailed description or claims (e.g., A or B) it is intended to mean "A or B or both". When the applicants intend to indicate "only A or B but not both" then the phrase "only A or B but not both" will be used. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is used herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be used.

What is claimed is:

1. A non-transitory computer storage medium storing computer-executable instructions that when executed by a processor of a computing device cause the processor to perform:
   identifying a unit of work key that is predefined for a program, where the program processes data from a data source, and further where the data source comprises one or more source tables and the unit of work key comprises one or more columns in the source tables;
   accessing a unit of work driver table that records unit of work key values for records in the data source that have been created, modified, or deleted in any source table since a last time the program was executed to determine a unique set of unit of work key values;
   selecting a set of records by creating a view query that selects, for a view, records from each source table that have the unit of work key values in the unit of work driver table; and
   providing the view of the selected records to the program.

2. The non-transitory computer storage medium of claim 1, where the program accesses the view as source data.

3. The non-transitory computer storage medium of claim 1, further comprising instructions that when executed cause the processor to populate the unit of work driver table by:
   accessing a program tracking table that records a last source modification time corresponding to a timestamp of the data source when the program was last executed; and
   identifying the unique set of respective unit of work key values for records in the data source having a last modification time that is later than the recorded last source modification time.

4. The non-transitory computer storage medium of claim 1, where the unit of work driver table comprises a source tracking table populated by a data management program that manages the data source, and where the source tracking table records unit of work key values for records that have been created, modified, or deleted since a last time the program was executed.

5. The non-transitory computer storage medium of claim 1, where the view query selects all records having a unit of work key in common with any record that has been created, modified, or deleted since a last time the program was executed.

6. The non-transitory computer storage medium of claim 1, where the program processes the selected records and populates a target table, where the instructions further comprise instructions for causing the processor to delete a record from the target table when:
   the record has a unit of work key value in the set of unique work key values; and
   the record has not been created, modified, or refreshed by execution of the program in the target table.

7. The non-transitory computer storage medium of claim 1 where the instructions for identifying comprise instructions for accepting an input of the unit of work key for the program from a user or an external function that selects the unit of work key for the program.

8. The non-transitory computer storage medium of claim 1, where the unit of work key comprises a first key and a second key, where the program inputs records from at least a first table comprising the first key and the second key and a second table comprising the first key and not the second key, and further comprising instructions for:
   accessing the unit of work driver table to determine:
      a unique set of unit of work first key value and second key value pairs for records in the first table that have been created, modified, or deleted since a last time the program was executed; and
      a unique set of unit of work first key values for records in the second table that have been created, modified, or deleted since the last time the program was executed; and
   creating a view query that:
      selects records in the first table that have the first key value and second key value pairs determined in the first table or that have the first key values determined in the second table;
      selects records in the second table that have the first key values determined in the first table or that have the first key values determined in the second table.

9. A computing system, comprising:
   a processor connected to a memory;
   a non-transitory computer storage medium connected to a data communication path with at least the processor and the memory;
   an incremental processing logic stored in the non-transitory computer storage medium and including instructions executable by the processor to cause the processor to identify a unit of work key that is predefined for a program, where the program is executable by the computing system to process data from a data source, and further where the data source comprises one or more source tables and the unit of work key comprises one or more columns in the source tables;
   a unit of work tracking logic stored in the non-transitory computer storage medium and including instructions executable by the processor to cause the processor to:
      determine a unique set of unit of work key values for records in the data source that have been created, modified, or deleted since a last time the program was executed; and
      populate a unit of work driver table with the unique set of unit of work key values;
   a view logic stored in the non-transitory computer storage medium and including instructions executable by the processor to cause the processor to:
      create a view that accesses the unit of work driver table to select a set of records from the data source that have the determined unit of work key values; and
      where the program, during execution of the program, reads input from the view to perform processing of data from the data source.

10. The computing system of claim 9, where the unit of work driver table comprises
   one or more source tracking tables populated by a data management program that manages the data source, where the source tracking tables record respective unique unit of work key values for records in the data source
   that have been created, modified, or deleted since the last time the program was executed.

11. The computing system of claim 9, where the incremental processing logic comprises:
   a program tracking logic configured to access a program tracking table that records a last execution time of the program; and
   and where the unit of work tracking logic is configured to identify respective unit of work key values for respective records in the data source having a last modification time that is later than the recorded last execution time and populate the unit of work driver table with the identified unit of work key values.

12. The computing system of claim 9, where the program processes the selected set of records and populates a target table, and where the incremental processing logic comprises a delete post processing logic configured to delete a record from the target table when:
   the record has a unit of work key value in the set of unique work key values; and
   the record has not been created, modified, or refreshed by execution of the program in the target table.

13. A computer-implemented method comprising:
   identifying a unit of work key that is predefined for a program, where the program processes data from a data source, and further where the data source comprises one or more source tables and the unit of work key comprises one or more columns in the source tables;
   accessing a unit of work driver table that records unit of work key values for records in the data source that have been created, modified, or deleted in any source table since a last time the program was executed to determine a unique set of unit of work key values;
   selecting a set of records by creating a view query that selects, for the view, records from each source table that have the unit of work key values in the unit of work driver table; and
   providing the view of the selected records to the program.

14. The computer-implemented method of claim 13, where the program accesses the view as source data.

15. The computer-implemented method of claim 13, further comprising populating the unit of work driver table by:
   accessing a program tracking table that records a last source modification time corresponding to a timestamp of the data source when the program was last executed; and
   identifying the unique set of respective unit of work key values for records in the data source having a last modification time that is later than the recorded last source modification time.

16. The computer-implemented method of claim 13, where the unit of work driver table comprises a source tracking table populated by a data management program that manages the data source, and where the source tracking table records unit of work key values for records that have been created, modified, or deleted since a last time the program was executed.

17. The computer-implemented method of claim 13, where the view query selects all records having a unit of work key in common with any record that has been created, modified, or deleted since a last time the program was executed.

18. The computer-implemented method of claim 13, where the program processes the selected records and populates a target table, where the method further comprises deleting a record from the target table when:
   the record has a unit of work key value in the set of unique work key values; and
   the record has not been created, modified, or refreshed by execution of the program in the target table.

19. The computer-implemented method of claim 13, where the unit of work key comprises a first key and a second key, where the program inputs records from at least a first table comprising the first key and the second key and a second table comprising the first key and not the second key, the method further comprising:
   accessing the unit of work driver table to determine:
      a unique set of unit of work first key value and second key value pairs for records in the first table that have been created, modified, or deleted since a last time the program was executed; and
      a unique set of unit of work first key values for records in the second table that have been created, modified, or deleted since the last time the program was executed; and
   creating a view query that selects:
      records in the first table that have the first key value and second key value pairs determined in the first table or that have the first key values determined in the second table; and
      records in the second table that have the first key values determined in the first table or that have the first key values determined in the second.

20. A non-transitory computer storage medium storing computer-executable instructions executable by a processor of a computing device to cause the processor to:
   identify a unit of work key that is predefined for a program, where the program processes data from a data source;
   access a program tracking table that records a last source modification time corresponding to a timestamp of the data source when the program was last executed; and
   identify a unique set of respective unit of work key values for records in the data source having a last modification time that is later than the recorded last source modification time;
   select a set of records from the data source that have the unit of work key values; and
   provide the selected set of records to the program.

21. The non-transitory computer storage medium of claim 20, where the data source comprises one or more source files and the unit of work key comprises one more fields in the source files.

22. The non-transitory computer storage medium of claim 20, where the data source comprises one or more source files and the unit of work key comprises one more fields in the source files.

23. The non-transitory computer storage medium of claim 20, where determining comprises instructions for causing the processor to execute a view query on the data source that selects all records having a unit of work key in common with any record that has been created, modified, or deleted since a last time the program was executed.

24. The non-transitory computer storage medium of claim 20, where the program is executable to process the selected records and populate a target table, where the instructions further comprise instructions for causing the processor to delete a record from the target table when:
   the record has a unit of work key value in the set of unique work key values; and
   the record has not been created, modified, or refreshed by execution of the program in the target table.

25. The non-transitory computer storage medium of claim 20, where the unit of work key comprises a first key and a second key, where the program inputs records from at least a first table comprising the first key and the second key and a second table comprising the first key and not the second key and further where:
   the instructions for determining comprise instructions for causing the processor to:
      determine a unique set of unit of work first key value and second key value pairs for records in the first table that have been created, modified, or deleted since a last time the program was executed; and
      determine a unique set of unit of work first key values for records in the second table that have been created, modified, or deleted since the last time the program was executed;
   the instructions for selecting comprise instructions for causing the processor to:
      select records in the first table that have the first key value and second key value pairs determined in the first table or that have the first key values determined in the second table;
      select records in the second table that have the first key values determined in the first table or that have the first key values determined in the second table; and
   the instructions for providing comprise instructions for causing the processor to provide the selected sets of records to the program.

26. A computing system, comprising:
   a processor connected to a memory;
   a non-transitory computer storage medium connected to a data communication path with at least the processor and the memory;
   an incremental processing logic stored in the non-transitory computer storage medium as instructions executable by the processor to cause the processor to:
      identify a unit of work key that is predefined for a program, where the program processes data from a data source that comprises one or more source tables and further where the unit of work key comprises one or more columns in the source tables; and
   a view logic stored in the non-transitory computer storage medium as instructions executable by the processor to cause the processor to:
      create a view that i) accesses one or more source tracking tables that record respective unique unit of work key values for records in the data source and a latest modification time for records having the respective unit of work key values and ii) selects records from the source table that have unit of work key values in the one or more source tracking tables that have been created, modified, or deleted since the last time the program was executed; and
      where the program reads input from the view to perform processing.

27. The computing system of claim 26, where the program is executable to process the selected records and populates a target table, and where the incremental processing logic comprises a delete post processing logic configured to delete a record from the target table when:
   the record has a unit of work key value in the set of unique work key values; and
   the record has not been created, modified, or refreshed by execution of the program in the target table.

28. A computer-implemented method, comprising:
   identifying, by a processor of a computing device, a unit of work key that is predefined for a program, where the program processes data from a data source;

accessing, by the processor, a program tracking table that records a last source modification time corresponding to a timestamp of the data source when the program was last executed; and identifying, by the processor, a unique set of respective unit of work key values for records in the data source having a last modification time that is later than the recorded last source modification time;

selecting, by the processor, a set of records from the data source that have the unit of work key values; and providing, by the processor, the selected set of records to the program.

29. The computer-implemented method of claim 28, where the data source comprises one or more source files and the unit of work key comprises one more fields in the source files.

30. The computer-implemented method of claim 28, where the data source comprises one or more source files and the unit of work key comprises one more fields in the source files.

31. The computer-implemented method of claim 28, where determining comprises executing a view query on the data source that selects all records having a unit of work key in common with any record that has been created, modified, or deleted since a last time the program was executed.

32. The computer-implemented method of claim 28, where the program processes the selected records and populates a target table, further comprising deleting a record from the target table when:
the record has a unit of work key value in the set of unique work key values; and
the record has not been created, modified, or refreshed by execution of the program in the target table.

33. The computer-implemented method of claim 28, where the unit of work key comprises a first key and a second key, where the program inputs records from at least a first table comprising the first key and the second key and a second table comprising the first key and not the second key and further where:
determining comprises:
determining a unique set of unit of work first key value and second key value pairs for records in the first table that have been created, modified, or deleted since a last time the program was executed; and
determining a unique set of unit of work first key values for records in the second table that have been created, modified, or deleted since the last time the program was executed;
selecting comprises:
selecting records in the first table that have the first key value and second key value pairs determined in the first table or that have the first key values determined in the second table;
selecting records in the second table that have the first key values determined in the first table or that have the first key values determined in the second table; and
providing comprises providing the selected sets of records to the program.

34. A non-transitory computer storage medium storing computer-executable instructions executable by a processor of a computing device to cause the processor to:
identify a unit of work key that is predefined for a program, where the program processes data from a data source;
determine a unique set of unit of work key values for records in the data source that have been created, modified, or deleted since a last time the program was executed by accessing a source tracking table populated by a data management program that manages the data source, where the source tracking table records unit of work key values for records that have been created, modified, or deleted since a last time the program was executed;
select a set of records from the source tracking table that have the unit of work key values; and
provide the selected set of records to the program.

35. The non-transitory computer storage medium of claim 34, where the data source comprises one or more source files and the unit of work key comprises one more fields in the source files.

36. The non-transitory computer storage medium of claim 34, where determining comprises executing a view query on the data source that selects all records having a unit of work key in common with any record that has been created, modified, or deleted since a last time the program was executed.

37. The non-transitory computer storage medium of claim 34, where the program processes the selected records and populates a target table, where the instructions further comprise instructions for deleting a record from the target table when:
the record has a unit of work key value in the set of unique work key values; and
the record has not been created, modified, or refreshed by execution of the program in the target table.

38. The non-transitory computer storage medium of claim 34, where the unit of work key comprises a first key and a second key, where the program inputs records from at least a first table comprising the first key and the second key and a second table comprising the first key and not the second key and further where:
the instructions for determining comprise instructions for:
determining a unique set of unit of work first key value and second key value pairs for records in the first table that have been created, modified, or deleted since a last time the program was executed; and
determining a unique set of unit of work first key values for records in the second table that have been created, modified, or deleted since the last time the program was executed;
the instructions for selecting comprise instructions for:
selecting records in the first table that have the first key value and second key value pairs determined in the first table or that have the first key values determined in the second table;
selecting records in the second table that have the first key values determined in the first table or that have the first key values determined in the second table; and
the instructions for providing comprise instructions for providing the selected sets of records to the program.

39. A computing system, comprising:
a processor connected to a memory;
a non-transitory computer storage medium connected to a data communication path with at least the processor and the memory;
an incremental processing logic stored in the non-transitory computer storage medium as instructions executable by the processor to cause the processor to:
identify a unit of work key that is predefined for a program, where the program processes data from a data source that comprises one or more source tables and further where the unit of work key comprises one or more columns in the source tables; and a view logic stored in the non-transitory computer storage medium as instructions executable by the processor to cause the processor to:
  create a view that i) accesses a program tracking table that records a last source modification time corresponding to a timestamp of the data source when the program was last executed and ii) selects records from the program tracking table that have unit of work key values in the one or more source tracking tables that have been created, modified, or deleted since the last time the program was executed; and
  where the program reads input from the view to perform processing.

40. The computing system of claim 39, where the program processes the selected records and populates a target table, and where the incremental processing logic comprises a delete post processing logic configured to delete a record from the target table when:
  the record has a unit of work key value in the set of unique work key values; and
  the record has not been created, modified, or refreshed by execution of the program in the target table.

41. A computer-implemented method, comprising:
  identifying, by a processor of a computing device, a unit of work key that is predefined for a program, where the program is executable by the computing device to process data from a data source;
  determining, by a processor, a unique set of unit of work key values for records in the data source that have been created, modified, or deleted since a last time the program was executed by accessing a source tracking table populated by a data management program that manages the data source, where the source tracking table records unit of work key values for records that have been created, modified, or deleted since a last time the program was executed;
  selecting, by a processor, a set of records from the source tracking table that have the unit of work key values; and
  providing, by a processor, the selected set of records to the program.

42. The non-transitory computer storage medium of claim 41, where the data source comprises one or more source files and the unit of work key comprises one more fields in the source files.

43. The non-transitory computer storage medium of claim 41, where determining comprises executing a view query on the data source that selects all records having a unit of work key in common with any record that has been created, modified, or deleted since a last time the program was executed.

44. The non-transitory computer storage medium of claim 41, where the program processes the selected records and populates a target table, where the instructions further comprise instructions for deleting a record from the target table when:
  the record has a unit of work key value in the set of unique work key values; and
  the record has not been created, modified, or refreshed by execution of the program in the target table.

45. The non-transitory computer storage medium of claim 41, where the unit of work key comprises a first key and a second key, where the program inputs records from at least a first table comprising the first key and the second key and a second table comprising the first key and not the second key and further where:
  the instructions for determining comprise instructions for:
    determining a unique set of unit of work first key value and second key value pairs for records in the first table that have been created, modified, or deleted since a last time the program was executed; and
    determining a unique set of unit of work first key values for records in the second table that have been created, modified, or deleted since the last time the program was executed;
  the instructions for selecting comprise instructions for:
    selecting records in the first table that have the first key value and second key value pairs determined in the first table or that have the first key values determined in the second table;
    selecting records in the second table that have the first key values determined in the first table or that have the first key values determined in the second table; and
  the instructions for providing comprise instructions for providing the selected sets of records to the program.

* * * * *

UNITED STATES PATENT AND TRADEMARK OFFICE
CERTIFICATE OF CORRECTION

PATENT NO. : 9,454,557 B2  
APPLICATION NO. : 14/158964  
DATED : September 27, 2016  
INVENTOR(S) : Rees et al.

Page 1 of 1

It is certified that error appears in the above-identified patent and that said Letters Patent is hereby corrected as shown below:

In the Claims

In Column 18, Line 4, in Claim 11, delete "and where" and insert -- where --, therefor.

In Column 19, Line 24, in Claim 19, delete "second." and insert -- second table. --, therefor.

Signed and Sealed this
Thirteenth Day of June, 2017

Joseph Matal
*Performing the Functions and Duties of the
Under Secretary of Commerce for Intellectual Property and
Director of the United States Patent and Trademark Office*